United States Patent [19]

Fukawa et al.

[11] Patent Number: 4,931,530

[45] Date of Patent: Jun. 5, 1990

[54] NOVEL AROMATIC POLYETHER AND A PROCESS FOR PRODUCING AN ETHER

[75] Inventors: Isaburo Fukawa; Tsuneaki Tanabe, both of Fuji, Japan

[73] Assignee: Asahi Kasei Kogyo Kabushiki Kaisha, Osaka, Japan

[21] Appl. No.: 410,029

[22] Filed: Sep. 20, 1989

Related U.S. Application Data

[63] Continuation of Ser. No. 114,744, Oct. 30, 1987, abandoned.

[30] Foreign Application Priority Data

Nov. 20, 1986 [JP] Japan .................................. 61-275312
Apr. 9, 1987 [JP] Japan .................................. 62-85708
Apr. 9, 1987 [JP] Japan .................................. 62-85709

[51] Int. Cl.$^5$ ...................... C08G 8/02; C08G 14/00
[52] U.S. Cl. .................................... 528/125; 528/126; 528/128; 528/219
[58] Field of Search ................ 528/125, 126, 128, 219

[56] References Cited

U.S. PATENT DOCUMENTS 3,065,205 11/1962 Bonner ................................ 528/180
4,668,744 6/1987 Matzner et al. ..................... 528/125

FOREIGN PATENT DOCUMENTS 55-13702 1/1980 Japan .
WO84/03891 10/1984 PCT Int'l Appl. .

Primary Examiner—John Kight, III
Assistant Examiner—M. L. Moore
Attorney, Agent, or Firm—Birch, Stewart, Kolasch & Birch

[57] ABSTRACT

There are disclosed a process for producing an aromatic (poly)etherketone or an aromatic (poly)ethersulfone having an ether group represented by the formula —Y—Ar—O—Ar—Y— which process comprises reacting an aromatic halogen compound having at least one active halogen group represented by the formula —Y—Ar—X, where Y denotes a ketone group or a sulfone group; Ar denotes a phenylene group or a nuclear-substituted product thereof; and X denotes a halogen atom which is bonded at the ortho- or para-position relative to Y, with a specified salt of an alkali metal, and an aromatic polyetherketone polymer which has a repeating unit represented by formula (I)

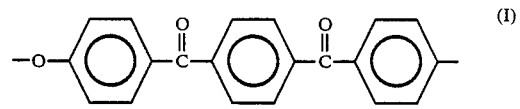

and which has a crystalline melting point not lower than 390° C. and an intrinsic viscosity of 0.7 to 2.0 dl/g (sulfuric acid at 25° C.).

16 Claims, No Drawings

NOVEL AROMATIC POLYETHER AND A PROCESS FOR PRODUCING AN ETHER

This application is a continuation of application Ser. No. 114,744, filed on Oct. 30, 1987, now abandoned.

BACKGROUND OF THE INVENTION

1. Field of the Invention

The present invention relates to a novel process for producing aromatic (poly)ether-ketones and -sulfones. As used herein, the term "(poly)ether" designates "ether" or "polyether". Further, the present invention relates to a novel crystalline, high melting point aromatic polyetherketones.

2. Discussion of Related Art

A typical prior method for producing an aromatic ether-ketone and -sulfone comprises reacting a halide represented by the formula —Y—Ar—X, wherein Y denotes a ketone group or a sulfone group; Ar denotes a phenylene group or a nuclear-substituted product thereof; and X denotes a halogen atom, the halogen atom being bonded at the ortho- or para-position relative to Y, with a phenol represented by the formula —Ar'—OH, wherein —Ar' denotes a phenylene group, in the presence of alkali, as expressed by the following equation.

By a similar method, an aromatic polyetherketone or -sulfone has been synthesized from an aromatic dihalide and a bisphenol.

However, the above-mentioned method which utilizes a nucleophilic reaction has the following disadvantages: it requires two types of raw materials (namely, an aromatic halide and a phenol); since the reaction is carried out at a high temperature in the presence of alkali, undesirable side reactions of a phenol are apt to take place; in the synthesis of polyether-ketone and -sulfone, a high molecular weight product cannot be obtained unless the molar ratio between an aromatic dihalide and a phenol is strictly adjusted; further, since a thermally unstable hydroxy phenyl group is contained in about half of the polymer terminals, a terminal group-stabilizing treatment is required. Moreover, although, in this nucleophilic polymerization, it is possible to produce a polymer having a repeating unit of the formulae (II) or (III)

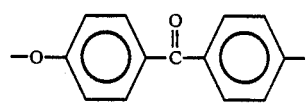

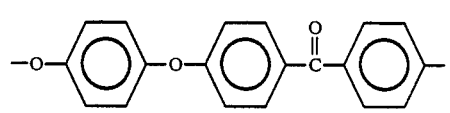

as disclosed in Japanese Patent Application Kokoku (Post-Exam. Publn.) Nos. 22,938/82 and 32,642/85, in order to produce a polymer which has a higher ketone-group content, higher melting point and greater heat resistance, for example, a polymer having a repeating unit represented by formula (IV)

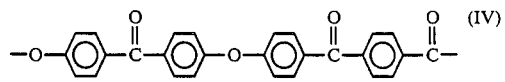

it is necessary to use a bisphenol of low reactivity

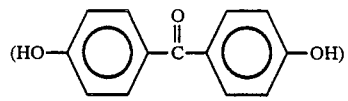

and hence would necessitate the use of severe reaction conditions. As a result, a branching and/or gellation of the polymer chain takes place in the prior method and hence the intended linear polymer cannot be produced [Japanese Patent Application Kokai (Laid-Open) No. 96,700/77]. Further, when it was intended to synthesize a polymer with a still higher ketone content having a repeating unit of formula (I)

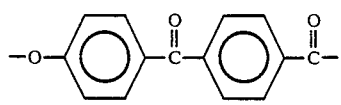

a bisphenol of a still lower reactivity

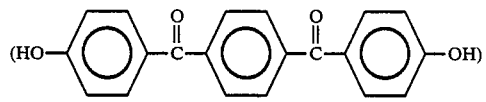

had to be used and a high molecular weight polymer could not be obtained.

On the other hand, apart from the above-mentioned method utilizing a nucleophilic reaction, a so-called Friedel-Crafts reaction method is known [Japanese Patent Application Kokoku (Post-Exam. Publn.) No. 34,419/81] which comprises forming a ketone group and sulfone group by means of an electrophilic reaction to produce an aromatic (poly)ether-ketones and -sulfones.

Since the former method and the latter method differ fundamentally one from the other in their reaction mechanism, the properties of the resulting polymers also differ one from the other. For example, a polymer obtained by the latter Friedel-Crafts reaction having the repeating unit of formula (II),

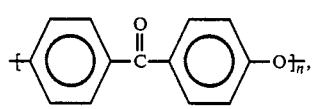

has a low crystallinity as compared with a polymer

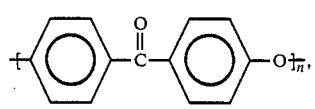

obtained by the former nucleophilic reaction, and as a consequence, has a disadvantage of having a low modulus at such high temperatures as 200° to 350° C. and of an extremely high heat shrinkage of stretched film. This is because, while para-linkages are exclusively formed in a nucleophilic reaction, ortho and meta- linkages are formed in addition to the para-linkage, resulting in abnormal linkages and/or branching taking place in the polymer chain. Polymers having such abnormal linkages are poor in mechanical properties and, to secure the desired properties, must have a particularly high molecular weight, which, however, inevitably causes lowering in moldability and crystallinity.

Using the Friedel-Crafts reaction, there has been prepared a polyetherketone of a higher melting point having the structural formula

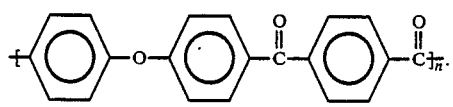

However, this polymer contains abnormal linkages, is thermally unstable and hence cannot undergo thermoplastic processing. Moreover, in the reaction, an unstable xantohydrol group is formed at the polymer terminal during polymerization. Accordingly, a special operation involving a reduction treatment of the xantohydrol group is necessary for stabilizing the polymer [Japan - US Polymer Symposium, 259 (1985)]. Further, since the polymer contains abnormal linkages, in spite of its ketone content, it still has a low melting point. Thus, a value as low as 385° C. has been solely reported for the polymer having repeating unit (I) [Japan - US Polymer Symposium, 259 (1985)].

Moreover, although usually HF-BF$_3$ is used as the polymerization catalyst and solvent in the Friedel-Crafts reaction, HF-BF$_3$ is unsuitable for commercial production since it is a very poisonous and corrosive substance. On the other hand, when another commonly used catalyst, aluminum chloride, is used, it has the defect of being more apt to form abnormal linkages and branching in the polymer structure than the above-mentioned HF-BF$_3$ system. Further, the resulting polymer is contaminated with aluminum chloride, which can only be difficultly removed, and hence is inevitably poor in thermal stability.

Thus, aromatic polyetherketones obtained by the Friedel-Crafts reaction are different in polymer structure from their equivalent which had been obtained by a nucleophilic polymerization and also are poorer in practical properties. Accordingly, they have not yet been produced commercially.

Referring further to the related art, it has been reported that an aliphatic carbonate is formed when an aliphatic halide and an alkali metal carbonate are reacted in the presence of a cyclic ether [K. Sogs, J. Polymer Sci., Lett., 15, 611 (1977)]. In Example 17 of Japanese Patent Application Kokai (Laid-Open) No. 129,294/78 invented by the named author, polycarbonate having a molecular weight of 8,000 has been obtained by reacting dichlorodiphenylsulfone with potassium carbonate in the presence of 18-crown-6-ether at 160° C. for 48 hours.

SUMMARY OF THE INVENTION

The object of the present invention is to provide a process for producing an aromatic ether which uses one type of raw material and is less susceptible to side reactions and also to provide a crystalline, high melting point aromatic polyetherketones having only a small amount of structural defects and which is obtainable by the process.

The present inventors have made extensive studies to attain the above object. As a result, it has been found that an aromatic (poly)ether-ketone and—sulfone can be produced by reacting an aromatic compound having a halogen atom activated by a ketone or a sulfone group with an alkali metal carbonate, bicarbonate, phosphate or stannate and optionally in the presence of a specified catalyst or additionally a co-catalyst. The present invention has been accomplished on the basis of the above findings.

Thus, the present invention provides a process for producing an aromatic (poly)etherketones and an aromatic (poly)ethersulfones which comprises reacting an aromatic halogen compound containing at least one activated halogen group represented by the formula —Y—Ar—X, wherein Y denotes a ketone group or sulfone group; Ar denotes a phenylene group or its nuclear-substituted product; X denotes a halogen atom, the halogen atom being bonded at the ortho- or para-position relative to Y, with an alkali metal carbonate, bicarbonate, phosphate or stannate, to form the aromatic (poly)etherketones or aromatic (poly)ethersulfone having an ether group represented by the formula —Y—Ar—O—Ar—Y—. In this reaction, silica, silica-alumina, alumina, and titania are favorably used as a catalyst and copper, copper compounds, or alkali metal fluorides as a co-catalyst.

Further, the present invention provides an aromatic polyetherketone which has a repeating unit represented by the formula (I)

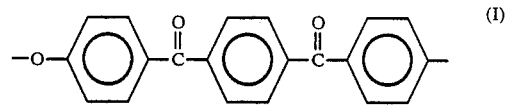

and which has a crystal melting point of not lower than 390° C. and an intrinsic viscosity of 0.7 to 2.0 dl/g (sulfuric acid at 25° C.), and also an aromatic polyetherketone copolymer which comprises a repeating unit represented by formula (I)

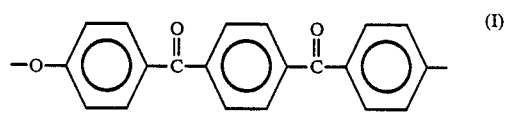

and a repeating unit represented by formula (II)

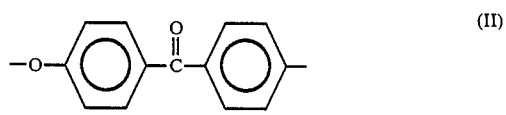

the ratio of unit (I) to unit (II) being in the range of (I):(II)=50:50 to 99:1, and which has a melting point not lower than 385° C. and an intrinsic viscosity of 0.7 to 2.0 dl/g (sulfuric acid at 25° C.).

DETAILED DESCRIPTION OF PREFERRED EMBODIMENTS

The ether-forming reaction according to the present invention will be illustrated with reference to specific examples, as expressed by the following reaction equations.

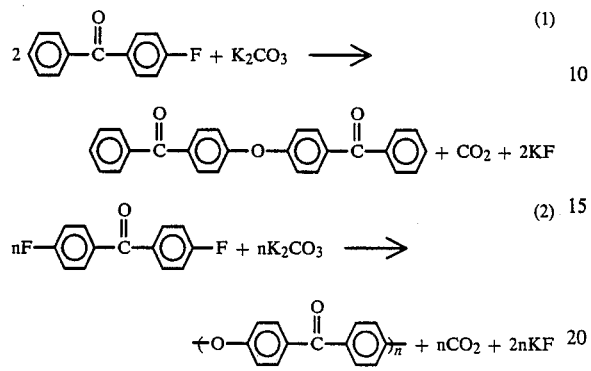

Thus, the oxygen in the ether linkage formed originates from $K_2CO_3$. In the reaction of an aromatic (di)halide with a (bis)phenol of the prior art, the oxygen in the ether linkage originates from the (bis)phenol. Although $K_2CO_3$ is used also in the prior reaction as the catalyst, its role is solely as a catalyst for forming the potassium salt of bis(phenol) in the polymerization, and hence is utterly different from $K_2CO_3$ serving as the reactant in the process of this invention.

(Prior Art)

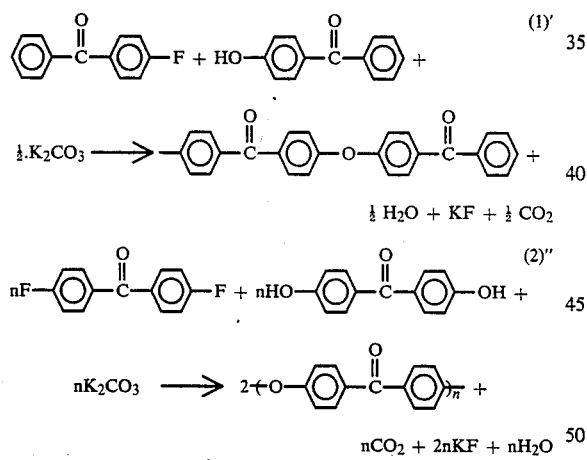

As the raw material for producing the ethers of the present invention, there should be used an aromatic halogen compound containing at least one functional group represented by the formula —Y—Ar—X, wherein Y denotes a ketone group or sulfone group; Ar denotes a phenylene group or its nuclear-substituted product; X denotes a halogen atom, the halogen atom being bonded at the ortho or para- position relative to Y. A halogen atom bonded at the ortho- or para-position relative to a ketone group or sulfone group is active and susceptible to a reaction, which makes ether linkage formation proceed smoothly.

Typical examples of such compounds may be represented by the following formulae:

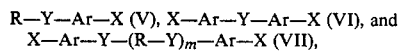

R—Y—Ar—X (V), X—Ar—Y—Ar—X (VI), and
X—Ar—Y—(R—Y)$_m$—Ar—X (VII), wherein R denotes, for example, an alkyl group such as $CH_3$— and —$CH_2$—, or an aromatic group such as

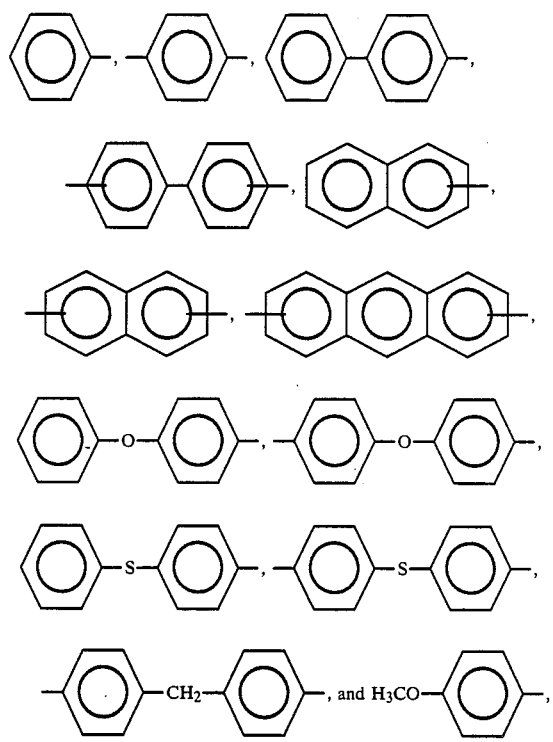

or a nuclear-substituted product thereof; m denotes an integer of 1 to 10; Y denotes a ketone group or sulfone group and, when two or more Y are present in one and the same molecule, they may be either the same or different from each other; and Ar denotes a phenylene group or a nuclear-substituted product thereof, the phenylene group being optionally condensed with Y (for example

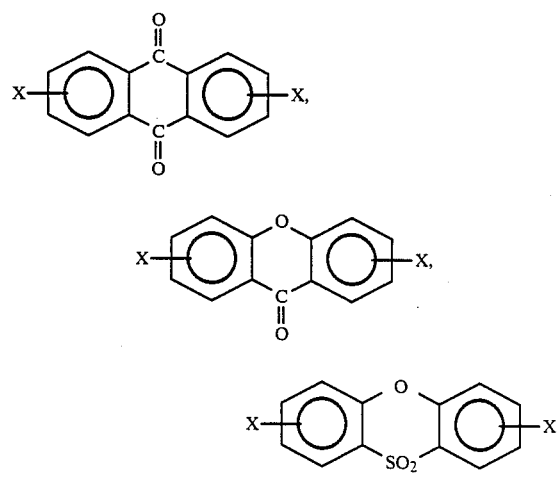

wherein X denotes a halogen atom and may be chlorine, fluorine, bromine or iodine).

For producing a polyether, such aromatic halogen compounds having two functional groups as those represented by the formula X—Ar—Y—Ar—X or X—Ar—Y—(R—Y)$_n$—Ar—X are used. When two or more types of such aromatic halogen compounds having two functional groups are used, a copolymer may be obtained. As a branching agent, aromatic halogen compounds having three functional groups are useful.

Specific examples of these compounds include 4-chlorobenzophenone, 2-chlorobenzophenone, 4,4'-dichlorobenzophenone, 4-chloroacetophenone, 4,4''-dichloroterephthalophenone (1,4-bis(4-chlorobenzoyl)-benzene), 4,4'-bis(4-chlorobenzoyl)diphenyl ether, 4,4''-dichloroisophthalophenone, 4-chlorodiphenyl sulfone, 4,4'-dichlorodiphenyl sulfone, 4-chlorophenylmethyl sulfone, 3-methyl-4-chlorobenzophenone, 3-methyl-4-chloroacetophenone, 4,4'-bis(4-chlorobenzenesulfonyl)-diphenyl ether, 4,4'-bis(4-chlorobenzenesulfonyl)biphenyl, 4,4'-bis(4-chlorobenzoyl)biphenyl, 4,4'-dichlorobenzyl, 4-fluorobenzophenone, 2-fluorobenzophenone, 4-fluoroacetophenone, 4,4'-difluorobenzophenone, 4,4''-difluoroterephthalophenone(1,4-bis(4-fluorobenzoyl)-benzene), 4,4'-bis(4-fluorobenzoyl)diphenyl ether, 4-fluorodiphenyl sulfone, 4,4'-difluorodiphenyl sulfone, 4-fluorophenylmethyl sulfone, 3-methyl-4-fluorobenzophenone, 4-methyl-2-fluorobenzophenone, 4,4'-bis(4-fluorobenzoyl)biphenyl, 4,4'-difluorobenzyl, 2,6-difluoroanthraquinone, and aromatic dihalides represented by the following formulae ally potassium salts have the advantage of giving a higher reaction velocity whereas sodium salts have the advantage of giving a less extent of side reactions. Mixtures of sodium salts with potassium salts may also be favorably used.

The molar ratio of aromatic halogen compounds to alkali metal salts is not specifically limited in the present invention. However, when, for example, an alkali metal carbonate is used, one atom of oxygen is released from one molecule of the alkali metal carbonate, while two atoms of halogen are eliminated from the aromatic halogen compound, to give rise to an ether-forming reaction. Accordingly, when it is intended to make the aromatic halogen compound react completely and to obtain an aromatic ether in a high yield, at least one equivalent of an alkali metal carbonate must be used for two halogen atoms present in the aromatic halogen compound.

However, using an amount of alkali metal carbonates which is too large, is disadvantageous from the viewpoint of production cost and, further, can sometimes cause undesirable side reactions. Preferred proportion of an alkali metal carbonate to be used is 0.1 to 10 equivalents relative to two halogen atoms present in the aromatic halogen compound. For obtaining a polymeric

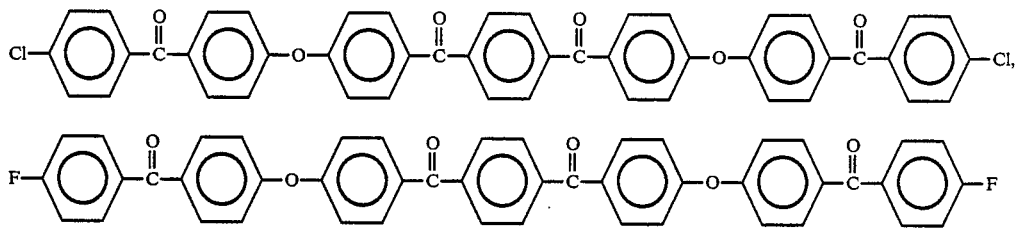

and further 4-bromobenzophenone, 4,4'-dibromobenzophenone, 4-iodobenzophenone, 4,4'-diiodobenzophenone etc. These may be used each alone or as a mixture thereof.

In the present invention, various types of aromatic halogen compounds may be used as described above. Among these, in general, the above-mentioned aromatic fluorine compounds have a high reactivity and can complete the reaction in a short length of time. Particularly, aromatic difluorides have an excellent characteristic property of yielding a high molecular weight polymer in a short time when used in the reaction of the present invention, but are expensive.

On the other hand, aromatic chlorine compounds can, though they are inferior in reactivity to aromatic fluorine compounds, give a desired product in a high yield when the catalyst or catalyst and co-catalyst according to the present invention are used. Particularly when aromatic dichlorides are used, high molecular weight polymers can be obtained. Since aromatic chlorine compounds are far more inexpensive than corresponding aromatic fluorine compounds, they are of industrial significance.

Example of alkali metal carbonates, bicarbonates, phosphates and stannates favorably used in this invention include potassium carbonate, sodium carbonate, lithium carbonate, cesium carbonate, rubidium carbonate, potassium bicarbonate, sodium bicarbonate, potassium phosphate, sodium phosphate, potassium stannate, sodium stannate, and the mixtures thereof. Particularly preferred are potassium salts and sodium salts. As to the comparison of potassium salts and sodium salts, generproduct, 0.9 to 2 equivalents are suitable.

It is possible to synthesize a compound or oligomer having a halogen at both terminals (Ex.

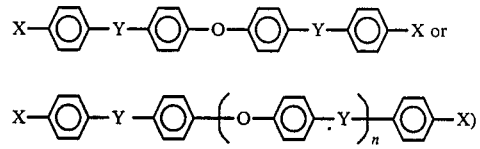

by using 1 equivalent or less of an alkali metal carbonate or by controlling the reaction conditions.

When an alkali metal bicarbonate is used as the alkali metal salt, two times the molar amount of an alkali metal carbonate is necessary for producing an equal amount of an ether. However, the reaction is faster than in the use of alkali metal carbonates.

These alkali metal salts give a higher reaction velocity when being used after finely pulverized.

The ether-forming reaction of the present invention can be promoted by using silica, silica-alumina, alumina or titania as a catalyst. The "silica" referred to herein includes various kinds of silica, such as silicon dioxide, silicic acid anhydride, silica, silica gel, dry process silica, fumed silica, wet process silica, silica precursor such as (organo)chlorosilanes, silicic acid, siloxanes and silicate, etc. The "silica-alumina" includes also such mineral-origin compounds as silica-alumina, zeolite, activated clay, sepiolite, montmorillonite, diatomaceous earth, etc. Among these, dry process silica (fumed silica), silica gel and silica-alumina, which have a small particle diameter and a large effective surface area, provide a particularly good effect.

The reaction proceeds faster when the catalyst is used after being finely pulverized. Although the amount of the catalyst to be added is not limited specifically, it is usually 0.1 to 100% by weight, preferably 1 to 30% by weight, based on the aromatic halogen compound of the raw material.

When the added amount is below the above value the addition of catalyst provides a poor effect; whereas addition of the catalyst in an amount larger than said value affords no more appreciable promotion of the ether-forming reaction and is sometimes unfavorable because it can cause an increase in the viscosity of the reaction system.

As the co-catalyst used in the present invention, there may be mentioned copper, copper compound or alkali metal fluoride. When a co-catalyst is used, the rate of reaction is further increased The use of these cocatalysts is particularly effective when an aromatic chlorine compound is used or when a sodium salt is used as the alkali metal salt. The co-catalyst may be used in a combination of two or more kinds thereof. The cocatalyst is practically ineffective in the absence of the catalyst.

Copper and the copper compounds used in the present invention are metallic copper and various types of cuprous and cupric compounds. There may be preferably used, for example, various types of cuprous halides such as cuprous chloride, cuprous bromide, and cuprous iodide; cupric halides such as cupric chloride and cupric bromide; cuprous oxide, cupric oxide, copper hydroxide, copper sulfate, basic copper carbonate, copper acetylacetonate, copper acetate and copper sulfide. These may also be used as a mixture thereof, and also either in an anhydrous form or in a form which contains water of crystallization. Alkali metal fluorides which may be favorably used are potassium fluoride and cesium fluoride. In the reaction of the aromatic chlorine compound with sodium carbonate, silica is preferably used as the catalyst and a copper compound as the co-catalyst.

Although the amount of the co-catalyst to be added is not specifically restricted, it is preferably 0.1 to 10% by weight based on the amount of the catalyst.

The co-catalyst may be either added to the reaction system simply together with the catalyst, or effectively used after being supported beforehand on the surface of the catalyst or after further roasted following the supporting. It is also effective to replace alkali metal ions with copper ions beforehand during the step of zeolite synthesis.

The reaction may be carried out either in the absence of a solvent or in the presence of a suitable solvent. There is no particular restriction as to the solvent which can be used in the reaction of the present invention and any desired solvent may be used so long as it is stable at the reaction temperature. There may be mentioned, for example, ketones such as acetophenone, benzophenone, xanthone and phenoxybenzophenone; sulfones such as sulfolane and diphenylsulfone; ethers such as diphenyl ether; amides such as N-methylpyrrolidone and hexamethylphosphoric triamide; hydrocarbons such as biphenyl, terphenyl, naphthalene and decalin; and halogenated hydrocarbons such as chlorinated biphenyl. Although the above examples refer to solvents which have a high boiling point and can be used for the reaction at normal pressure, it is also possible, for those solvents which have a lower boiling point than the reaction temperature, to carry out the reaction under elevated pressure.

The reaction proceeds more readily when the solvent used has a higher polarity. As examples of particularly preferable solvents, there may be mentioned diphenylsulfone, benzophenone, and xanthone, which have a high polarity and are stable at a high temperature.

Although the reaction temperature may vary depending on the type of the aromatic halogen compounds, of alkali metal salts, and of catalysts and co-catalysts, it is suitably 150° C. to 400° C. Below 150° C. the reaction is slow, whereas above 400° C. undesirable side reactions other than ether formation are apt to take place.

The polymer solution thus obtained may optionally be subjected to conventional terminal stabilizing reaction by means of an active halide compound such as 4-chlorobenzophenone and 4-chlorodiphenylsulphone in order to further improve the thermal stability thereof.

The polymer solution thus obtained is cooled and solidified. It is then pulverized and washed alternately with an organic solvent such as acetone and water to obtain a polymer. When removal of the silica is required, it can be accomplished by washing the polymer with an aqueous alkali solution. Copper compounds of the co-catalyst can be removed by treatment with nitric acid or various copper chelating agent-containing solutions.

Thus, according to the process of the present invention, various types of aromatic (poly)ethers are produced.

For example, from the aromatic halogen compounds represented by the following formulae (V), (VI) and (VII), are obtained the aromatic (poly)ethers represented by the general formulae (VIII), (IX) and (X), respectively.

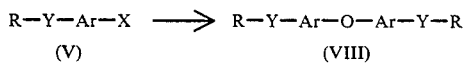
(V)　　　　　　　　(VIII)

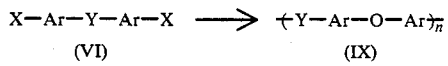
(VI)　　　　　　　　(IX)

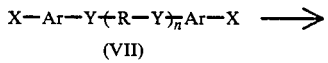
(VII)

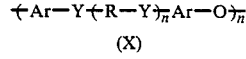
(X)

Particularly, according to the process of the present invention, novel polymers have been obtained which could not be synthesized previously. One of these is a polyetherketone having a high melting point and a high crystallinity not attainable previously and a copolymer thereof, which are obtained, for example, by the following reaction schemes shown below. The polyetherketone has a high melting point and good thermal stability as compared with those obtainable by conventional Friedel-Crafts reaction method and nucleophilic polymerization method. This is presumably because it contains less abnormal linkages than those obtainable by the previous methods and hence it has a more linear chain structure.

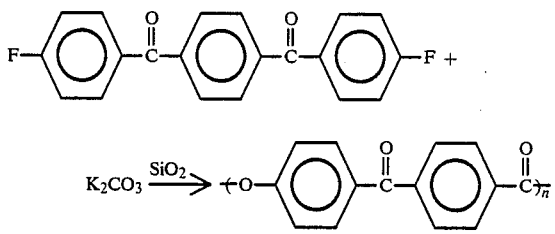

Typical example of the polymer:
Intrinsic viscosity 0.7 to 2.0 dl/g (sulfuric acid at 25° C.),
m.p. 390° C. or more

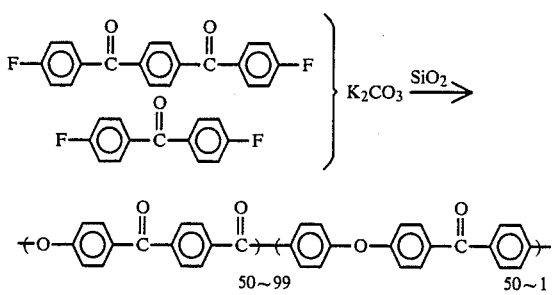

Typical example of the copolymer:
Intrinsic viscosity 0.7 to 2.0 dl/g
m.p. 385° C. or more The above-mentioned polymer and copolymer should have a molecular weight of 0.7 to 2.0 dl/g (sulfuric acid at 25° C.) in terms of intrinsic viscosity. When the intrinsic viscosity is less than 0.7 dl/g the product is brittle, whereas when it is above 2.0 dl/g (sulfuric acid at 25° C.) the product has a poor melt processability and a low crystallinity.

The polymerization according to the process of the present invention is carried out in a similar solvent to that used in conventional nucleophilic polycondensation and under alkaline conditions. Accordingly, the polymerization can be carried out in combination with prior nucleophilic polycondensation. For example, after a polymer has been produced by the process of the present invention, an aromatic dihalide, bisphenol and alkali catalyst may newly be added to effect polymerization. Also, these polymerizations may be carried out in the reverse order. Thus, it is also possible to obtain various types of copolymers (e.g. block copolymer) and polymer blends which have not been obtainable previously.

Since the process for producing aromatic (poly)ethers according to the present invention does not use unstable phenol, it produces very little by-products. Further, since it requires only one type of raw material, it has an advantage in that the necessary raw material can be secured easily. Further, it provides a high melting point, highly crystalline, linear polyetherketone substantially free from abnormal linkages, such not having previously been obtainable.

The aromatic (poly)ethers obtained according to the process of the present invention are useful as resin materials, sensitizers, raw materials for pharmaceuticals and agricultural chemicals, solvents, heating medium, etc.

Particularly, aromatic polyetherketones of high molecular weights are useful as high performance engineering plastics having excellent in heat resistance, mechanical non-flammability properties, etc.

The polymer of the present invention can be used in any desired form, for example as injection molded articles, extrusion molded articles, coatings, films and fibers. Further, it can be mixed with various heat resistant engineering plastics (e.g. polyetherketone, polyethersulfone, polyetherimide, aromatic polyester and PPS), general-purpose engineering plastics, glass fiber, aramid fiber, carbon fiber, and inorganic materials, to be used in the form of polymer alloys and composite materials.

EXAMPLE 1

In a 50 ml flask are placed 5.00 g (0.023 mole) of 4,4'-difluorobenzophenone, 3.17 g (0.023 mole) of potassium carbonate and 5 g of benzophenone as a solvent. After the atmosphere is replaced with nitrogen, the mixture is brought to 300° C. over a period of 1 hour with stirring and allowed to react under the same conditions for 10 hours.

The reaction product is pulverized and then washed twice with acetone and twice with warm water to obtain 2.7 g of white powder. The product is, at room temperature, soluble in concentrated sulfuric acid, giving a yellow solution, but utterly insoluble in such organic solvents as chloroform, dimethylformamide, and N-methylpyrrolidone. The $^1$H-NMR spectrum of the product in deuterated sulfuric acid showed absorptions at 7.05 ppm (doublet) and at 7.75 ppm (doublet) originating from the structure

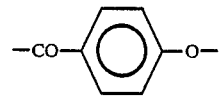

and absorptions at 7.65 ppm (multiplet) and at 7.00 ppm (triplet) originating from the structure

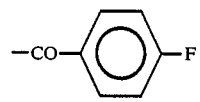

in an intensity ratio of about 3:1.

The infrared absorption spectrum, and the ultraviolet absorption spectrum in concentrated sulfuric acid, of the product coincided substantially with those of polyetherketone

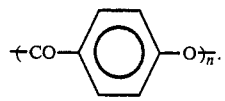

From the results obtained above, it is decided that the product of this Example is an oligoetherketone (tetramer on the average) which is represented by the following formula and whose both terminals are the fluorobenzoyl group.

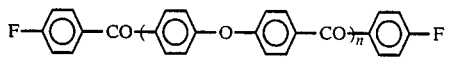

The ηsp/c of the product measured in 0.1 wt % solution in concentrated sulfuric acid at 25° C. is 0.09 dl/g.

EXAMPLE 2

The reaction is carried out in the same manner as in Example 1 except that the amount of potassium carbonate is changed to 6.9 g (0.05 mole) and the reaction time at 300° C. was altered to 12 hours to obtain 4.3 g of white powder.

The infrared absorption spectrum, and the ultraviolet absorption spectrum in sulfuric acid, of the product are approximately the same as those obtained in Example 1. However, absorptions at 7.65 ppm and 7.00 ppm in the $^1$H-NMR spectrum originating from the fluorobenzoyl group virtually disappeared. The ηsp/c determined in sulfuric acid is 0.57 dl/g.

Accordingly, the product of this Example is a polyetherketone having a higher molecular weight than that of the product of Example 1.

EXAMPLE 3

A reaction is carried out in the same manner as in Example 2 except that 7.4 g (0.023 mole) of 4,4″-difluoroterephthalophenone is used in place of 5.00 g of 4,4′-difluorobenzophenone and the amount of solvent, benzophenone, is altered to 10 g, to obtain 6.3 g of white powder. The product is also insoluble in organic solvents at room temperature, but dissolved in concentrated sulfuric acid to give a yellow solution. The ηsp/c is 0.3 dl/g measured in 0.1 wt % solution in concentrated sulfuric acid at 25° C.

The $^1$H-NMR spectrum of the product in deuterated sulfuric acid showed absorptions at 7.93 ppm (doublet) and 7.08 ppm (doublet) originating from

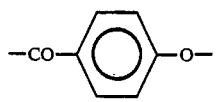

unit and an absorption at 7.77 ppm (singlet) originating from

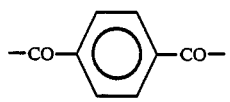

unit. Thus, the product is confirmed to be a polyetherketoneketone

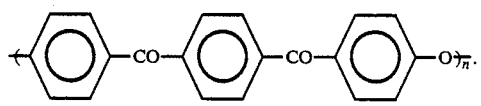

EXAMPLE 4

In a 20 ml flask are placed 5 g (0.02 mole) of 4,4′-difluorodiphenylsulfone and 2.8 g (0.02 mole) of potassium carbonate. After the atmosphere is replaced with nitrogen, the mixture is brought up to 300° C. over a period of 1 hour with stirring and allowed to react under the same conditions for 3 hours. After the reaction, the reaction mixture is a fairly viscous liquid even at 300° C. and, when cooled down to 200° C., the whole system solidified.

The reaction product is dissolved in 30 ml of N-methylpyrrolidone and then precipitated in a large amount of methanol to obtain 4.2 g of white solid. The solid is purified by repeating reprecipitation twice by means of N-methylpyrrolidone-methanol/water (50/50). The resulting product gave ηsp/c of 0.6 dl/g in 0.11 wt % solution in N-methylpyrrolidone. The infrared absorption spectrum of the film of the product obtained by casting from its N-methylpyrrolidone solution coincided completely with that of polyethersulfone

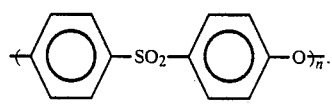

EXAMPLE 5

In a 100 ml flask are placed 10.91 g (0.05 mole) of 4,4′-difluorobenzophenone, 6.63 g (0.0625 mole) of sodium carbonate, 2.0 g of silica (Siloid 244, mfd. by Fuji-Davidson Co., Ltd.) and 40 g of diphenylsulfone. After the atmosphere is replaced with nitrogen, the mixture is brought to 250° C. in 30 minutes with stirring and kept at the temperature for 1.5 hours. Thereafter, the mixture is brought up to 315° C. over a period of 30 minutes and then allowed to react under the same conditions for 8 hours. The resulting product is pulverized and then washed twice with warm acetone, twice with warm water, 4% sodium hydroxide solution, water, and acetone to obtain a powder pale cream in color. The product gave ηsp/c of 1.15 dl/g as determined in 0.1 wt % solution in concentrated sulfuric acid and a crystalline melting point of 375° C. as determined by DSC (10° C./min).

EXAMPLE 6

In a 100 ml flask are placed 4.39 g (0.0201 mole) of 4,4′-difluorobenzophenone, 6.49 g (0.0201 mole) of 4,4′-difluoroterephthalophenone, 7.25 g (0.0684 mole) of sodium carbonate, 2.0 g of silica (Aerosil 300, mfd. by Nippon Aerosil Co., Ltd.) and 40 g of diphenylsulfone. After the atmosphere is replaced with nitrogen, the mixture is brought to 280° C. in 30 minutes with stirring and kept at the temperature for 1.5 hours. Thereafter, the mixture is brought to 325° C. over a period of 30 minutes and allowed to react at the temperature for 4.25 hours. The reaction product is washed in the same manner as in Example 5 to obtain a polymer pale cream in color. The polymer gave intrinsic viscosity of 0.85 dl/g in concentrated sulfuric acid at 25° C. and a crystalline melting point of 387° C. as determined by DSC (10° C./min). The elemental analysis, $^1$H-NMR and $^{13}$C-NMR of the polymer showed that it has a structure represented by the formula

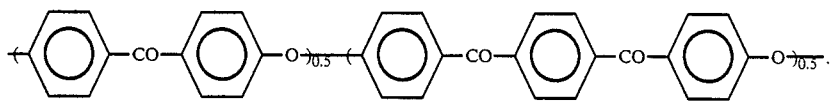

EXAMPLE 7

In a 100 ml flask are placed 10.73 g (0.033 mole) of 4,4'-difluoroterephthalophenone, 1.77 g (0.0167 mole) of sodium carbonate, 4.60 g (0.033 mole) of potassium carbonate, 1.0 g of silica (Aerosil 300, mfd. by Nippon Aerosil Co., Ltd.) and 40 g of diphenylsulfone. After the atmosphere is replaced with nitrogen, the mixture is brought to 285° C. in 30 minutes with stirring and kept at the temperature for 1.5 hours. Thereafter, the mixture is brought to 335° C. in 30 minutes and allowed to react at the temperature for 1.75 hours. The reaction product is washed in the same manner as in Example 5 to obtain a polymer pale cream in color. The polymer gave intrinsic viscosity of 0.95 dl/g in concentrated sulfuric acid at 25° C. and a crystalline melting point of 398° C. as determined by DSC (10° C./min). The elemental analysis, $^1$H-NMR and $^{13}$C-NMR of the polymer showed that it had a structure represented by the formula

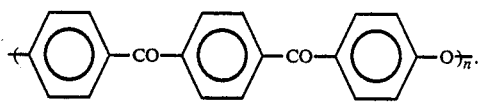

EXAMPLE 8

In a 200 ml flask are placed 21.4 g (0.03 mole) of the aromatic difluoride (A) obtained in Referential Example 1 described later, 6.21 g (0.045 mole) of potassium carbonate, 2.0 g of silica (Aerosil 300, mfd. by Nippon Aerosil Co., Ltd.) and 45 g of diphenylsulfone. After the atmosphere is replaced with nitrogen, the mixture is brought from room temperature to 310° C. over a period of 1 hour and allowed to react at the temperature for 0.5 hour.

Then, the reaction mixture is pulverized and washed with warm after and warm acetone three times to obtain 21.5 g of pale yellow solid. The product dissolved completely in concentrated sulfuric acid to give a yellow solution. The intrinsic viscosity is 1.15 measured in concentrated sulfuric acid at 25° C. The product gave a tough, pale yellow film when compressed at 400° C.

Referential Example 1

Preparation of aromatic difluoride (A)

(1) Synthesis of 4,4'-diphenoxyterephthalophenone

Into 350 ml of o-dichlorobenzene cooled at 0° C. are dissolved 20.3 g (0.1 mole) of terephthalic dichloride, 51.1 g (0.3 mole) of diphenyl ether and 26.6 g (0.2 mole) of aluminum chloride, and the mixture is allowed to react for 4.5 hours with stirring. Then the reaction mixture is added into a large amount of methanol-hydrochloric acid mixture. The resulting precipitated solid is collected by filtration and washed several times with water and methanol.

The product has a melting point of 218° C., which coincided with that of an authentic sample of 4,4'-diphenoxyterephthalophenone.

(2) Synthesis of aromatic difluoride (A)

Into 60 ml of o-dichlorobenzene are dissolved 4.7 g (0.01 mole) of 4,4'-diphenoxyterephthalophenone obtained above and 6.00 g (0.045 mole) of aluminum chloride. Then, 4.0 g (0.025 mole) of 4-fluorobenzoyl chloride is added dropwise to the solution mixture at room temperature with stirring. The resulting mixture is warmed gradually and allowed to react at 60° C. for 3 hours to complete the reaction. The reaction mixture is then added to a methanol-hydrochloric acid mixture. The precipitated solid is collected by filtration and purified by successive washing with water, acetone, N-methylpyrrolidone and acetone.

The product has a melting point of 308° C. and is confirmed by elemental analysis to be a compound represented by the formula

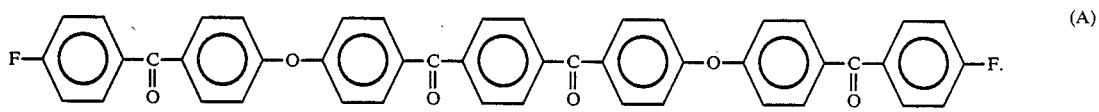

EXAMPLE 9

In a 200 ml flask are placed 20 g (0.10 mole) of 4-fluorobenzophenone, 13.8 g (0.10 mole) of finely pulverized potassium carbonate and 20 g of diphenylsulfone. After the atmosphere is replaced with nitrogen, the mixture is brought from room temperature up to 250° C. in 30 minutes with stirring and allowed to react as such as 250° C. for 2 hours. A part of the reaction mixture is dissolved in N-methylpyrrolidone and analyzed by means of liquid chromatography. The result obtained showed that conversion to 4,4'-dibenzoyldiphenylether is 20%.

EXAMPLE 10

The procedures of Example 9 are repeated except that 1.0 g of silica (Aerosil 300, mfd. by Nippon Aerosil Co.) is added as the catalyst. It was found that conversion to 4,4'-dibenzoyldiphenyl ether is 85%.

EXAMPLE 11

The procedures of Example 10 are repeated except that 20 g (0.10 mole) of 2-fluorobenzophenone is used in place of 20 g of 4-fluorobenzophenone. It is found that conversion to 2,2'-dibenzoyldiphenylether is 82%.

EXAMPLE 12

In a 200 ml flask are placed 20 g (0.092 mole) of 4-chlorobenzophenone, 12.7 g (0.092 mole) of finely pulverized potassium carbonate, 20 g of diphenylsulfone and 1 g of silica (Aerosil 300, mfd. by Nippon Aerosil Co., Ltd.). After the atmosphere is replaced with nitrogen, the mixture is brought from room temperature up to 300° C. in 30 minutes with stirring and allowed to react as such at 300° C. for 2 hours. A part of the reaction mixture is dissolved in N-methylpyrrolidone and analyzed by means of liquid chromatography. The result obtained showed that 80% of 4-chlorobenzophenone is changed into 4,4'-dibenzoyldiphenylether.

EXAMPLE 13

In a 200 ml flask are placed 20 g (0.092 mole) of 4-chlorobenzophenone, 18.4 g (0.184 mole) of potassium bicarbonate, 20 g of diphenylsulfone, and 1 g of silica alumina (aluminum silicate, mfd. by Wako Junyaku Kogyo K.K.). After the atmosphere is replaced with nitrogen, the mixture is brought up to 300° C. in 30 minutes with stirring and allowed to react as such as 300° C. for 2 hours. Analysis of the reaction mixture conducted in the same manner as in Example 1 showed that conversion to 4,4'-dibenzoyldiphenylether is 80%.

EXAMPLE 14

The procedures of Example 13 are repeated except that 9.8 g (0.092 mole) of sodium carbonate is used in place of 18.4 g of potassium bicarbonate. Conversion to 4,4'-dibenzoyldiphenylether is 60%.

EXAMPLES 15 to 19

Reactions and analysis are carried out in the same manner as in Example 12 except that 1.0 g of catalyst shown below is used in place of silica. Conversion from 4-chlorobenzophenone to 4,4'-dibenzoyldiphenylether is as shown in the following table.

| Example No. | | Catalyst | Conversion (%) |
|---|---|---|---|
| 15 | Silica-alumina | (Aluminum silicate, mfd. by Wako Junyaku Kogyo KK) | 80 |
| 16 | α-Alumina | (mfd. by Rare Metallic KK) | 40 |
| 17 | Titanium oxide | (Titanium Oxide P-25, mfd. by Nippon Aerosil Co.) | 50 |
| 18 | Activated clay | S-65, mfd. by Nippon Kassei Hakudo KK) | 60 |
| 19 | Zeolite | (TSZ-410-KOA, mfd. by Toyo Soda Mfg. Co., Ltd.) | 60 |

EXAMPLE 20

In a 200 ml flask are placed 20 g (0.092 mole) of 4-chlorobenzophenone, 9.75 g (0.092 mole) of finely pulverized sodium carbonate, 20 g of diphenylsulfone, 1.5 g of silica (Aerosil 300, mfd. by Nippon Aerosil Co.) and 0.5 g of anhydrous cupric chloride. After the atmosphere is replaced with nitrogen, the mixture is brought up to 300° C. in 30 minutes with stirring and allowed to react as such as 300° C. for 2 hours. A part of the reaction mixture is dissolved in N-methylpyrrolidone and analyzed by means of liquid chromatography. The result obtained showed that 86% of 4-chlorobenzophenone has been changed into 4,4'-dibenzoyldiphenylether. This conversion is higher than that in Example 14 wherein reaction is conducted under approximately the same conditions except that cupric chloride is not added.

EXAMPLES 21 to 29

Reactions and analysis are carried out in the same manner as in Example 20 except that 0.5 g of various copper compounds are added in place of 0.5 g of anhydrous cupric chloride used in Example 20. The results obtained are shown in Table 1.

TABLE 1

| Example No. | Additive | Conversion (%) |
|---|---|---|
| 21 | Cuprous bromide | 85 |
| 22 | Cupric hydroxide | 82 |
| 23 | Cuprous oxide | 77 |
| 24 | Cupric oxide | 74 |

TABLE 1-continued

| Example No. | Additive | Conversion (%) |
|---|---|---|
| 25 | Copper sulfate (penta-hydrate) | 82 |
| 26 | Basic copper carbonate | 82 |
| 27 | Cuprous chloride | 85 |
| 28 | Copper iodide | 72 |
| 29 | Metallic copper | 67 |

EXAMPLE 30

In a 200 ml flask are placed 20 g (0.092 mole) of 4-chlorobenzophenone, 9.75 g (0.092 mole) of finely pulverized sodium carbonate, 20 g of diphenylsulfone, 1.5 g of silica (Aerosil 300, mfd. by Nippon Aerosil Co.), 0.1 g of cuprous oxide and 0.5 g of potassium fluoride. After the atmosphere is replaced with nitrogen, the mixture is brought up to 300° C. in 30 minutes with stirring and allowed to react as such at 300° C. for 1 hour. A part of the reaction mixture is dissolved in N-methylpyrrolidone and analyzed by means of liquid chromatography. The result obtained showed that 83% of 4-chlorobenzophenone has changed into 4,4'-dibenzoyldiphenyl ether. Thus, a higher conversion is obtained in a short time as compared with Example 23 wherein reaction is conducted under approximately the same conditions except that potassium fluoride is not added.

EXAMPLE 31

In a 100 ml flask are placed 20 g (0.092 mole) of 4-chlorobenzophenone, 21.3 g (0.08 mole) of sodium stannate ($Na_2SnO_3 \cdot 3H_2O$) and 20 g of diphenyl sulfone. After the atmosphere is replaced with nitrogen, the mixture is brought from room temperature up to 300° C. in 30 minutes with stirring and allowed to react as such at 300° C. for 2 hours. A part of the reaction mixture is dissolved in N-methylpyrrolidone and analyzed by means of liquid chromatography. The result obtained showed that conversion to 4,4'-dibenzoyldiphenylether was 36%.

EXAMPLE 32

In a 200 ml flask are placed 20 g (0.092 mole) of 4-chlorobenzophenone, 16 g (0.08 mole) of potassium phosphate, 20 g of diphenylsulfone, 1.5 g of silica (Aerosil 300, mfd. by Nippon Aerosil Co.) and 0.5 g of anhydrous cupric chloride. After the atmosphere is replaced with nitrogen, the mixture is brought up to 300° C. in 30 minutes with stirring and allowed to react as such at 300° C. for 2 hours. A part of the reaction mixture is dissolved in N-methylpyrrolidone and analyzed by means of liquid chromatography. The result obtained showed that 81% of 4-chlorobenzophenone has changed into 4,4'-dibenzoyldiphenyl ether.

EXAMPLE 33

In a 200 ml flask were placed 24 g (0.092 mole) of 4-bromobenzophenone, 9.75 g (0.092 mole) of finely pulverized sodium carbonate, 20 g of diphenylsulfone, 1.5 g of silica (Aerosil 300, mfd. by Nippon Aerosil Co.) and 0.5 g of anhydrous cupric chloride. After the atmosphere is replaced with nitrogen, the mixture was brought up to 300° C. in 30 minutes with stirring and allowed to react as such at 300° C. for 30 minutes. A part of the reaction mixture is dissolved in N-methylpyrrolidone and analyzed by mean of liquid chromatography. The result obtained showed that 72% of 4-bromobenzophenone has changed into 4,4′-dibenzoyldiphenylether.

EXAMPLE 34

In a 100 ml flask are placed 10 g (0.040 mole) of 4,4′-dichlorobenzophenone, 8.28 g (0.060 mole) of potassium carbonate, 1.0 g of silica (Aerosil 300, mfd. by Nippon Aerosil Co.) and 15 g of diphenylsulfone. After the atmosphere is replaced with nitrogen, the mixture is brought to 300° C. over a period of 1 hour with stirring and allowed to react under the same conditions for 2 hours. The resulting product is pulverized and then washed twice with acetone, twice with warm water and further once with acetone to obtain 7.2 g of pale yellow powder. The $^1$H-NMR spectrum of the polymer showed that it is of the structure represented by

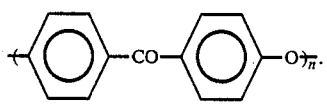

The ηsp/c of the polymer in concentrated sulfuric acid is 0.80 dl/g.

EXAMPLE 35

In a 1 stainless steel autoclave are placed 125 g (0.498 mole) of 4,4′-dichlorobenzophenone, 10 g of silica (siloid 244, mfd. by Fuji-Davidson Co.), 65.99 g (0.623 mole) of finely pulverized sodium carbonate, 0.27 g of anhydrous cupric chloride, and 430 g of diphenylsulfone. After the atmosphere is replaced with nitrogen, the inner temperature of the autoclave is brought to 310° C. and the mixture is allowed to react at the temperature for 6 hours. Thereafter, a molten mixture of 50 g of 4-chlorobenzophenone and 50 g of diphenylsulfone is added to the reaction mixture under nitrogen, and the whole is allowed to react for 30 minutes. After cooled, the contents of the autoclave is pulverized and washed with acetone, water, dilute nitric acid, aqueous sodium hydroxide solution, water and acetone to obtain 92 g of pale yellow powder. The polymer showed ηsp/c of 0.87 dl/g as determined in concentrated sulfuric acid and a crystalline melting point of 373° C. as determined by DSC.

EXAMPLE 36

A reaction is carried out in the same manner as in Example 35 except that the added amount of sodium carbonate is altered to 55.4 g (0.523 mole) and that of diphenylsulfone to 230 g, to obtain 91 g of pale yellow polymer. The polymer showed ηsp/c of 0.92 dl/g in concentrated sulfuric acid and a crystalline melting point of 372° C.

EXAMPLE 37

In a 100 ml flask are placed 10 g (0.0348 mole) of 4,4′-dichlorodiphenylsulfone, 5.77 g (0.042 mole) of potassium carbonate, 1.0 g of silica (Siloid 244, mfd. by Fuji-Davidson Co.) and 15 g of diphenylsulfone. After the atmosphere is replaced with nitrogen, the mixture is brought up to 300° C. in 1 hour with stirring and allowed to react under the same conditions for 6 hours.

The reaction product is dissolved in chloroform, the insolubles were filtered off, and the filtrate is poured into methanol to obtain 7.7 g of white polymer. The ηsp/c of the polymer in N-methylpyrrolidone was 0.45 dl/g. The infrared absorption spectrum of the film of the polymer obtained by casting from its N-methylpyrrolidone solution coincided completely with that of polyethersulfone

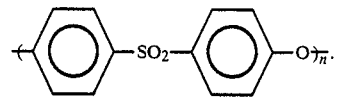

What is claimed is:

1. A process for producing an aromatic (poly)etherketone or an aromatic (poly)ethersulfone which comprises reacting an aromatic halogen compound containing at least one active halogen group represented by formula $$-Y-Ar-X,$$

wherein Y denotes a ketone group or a sulfone group; Ar denotes a phenylene group or a nuclear-substituted product thereof; and X denotes a halogen atom, the halogen atom being bonded at the ortho- or para-position relative to Y, with a salt of an alkali metal, in which said salt is an alkali metal carbonate, bicarbonate, phosphate, stannate or mixtures thereof, to form the aromatic (poly)etherketone or aromatic (poly)ethersulfone having an ether group represented by the formula 

2. The process according to claim 1 wherein X is a fluorine atom.

3. The process according to claim 2 wherein the reacting is conducted in the presence of a silica, silica-alumina, alumina, or titania catalyst.

4. The process according to claim 1 wherein X is a chlorine atom.

5. The process according to claim 4 wherein the reacting is conducted in the presence of a silica, silica alumina, alumina, or titania catalyst.

6. The process according to claim 5 wherein the reacting is conducted in the presence of a copper or a copper compound co-catalyst.

7. The process according to claim 5 wherein said salt of the alkali metal is sodium carbonate.

8. The process according to claim 7 wherein the reacting is conducted in the presence of an alkali metal fluoride co-catalyst.

9. An aromatic polyetherketone consisting of a repeating unit represented by formula (I)

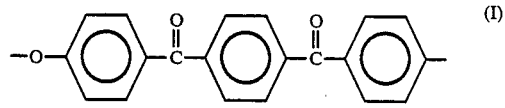

and which has a crystalline melting point not lower than 390° C. and an intrinsic viscosity of 0.7 to 2.0 dl/g (sulfuric acid at 25° C.

10. An aromatic polyetherketone copolymer consisting of a repeating unit represented by formula

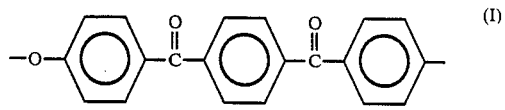

and a repeating unit represented by formula (II)

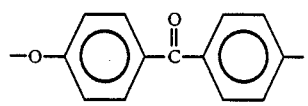

the ratio of the unit (I) to the unit (II) being in the range of (I):(II)=50:50 to 99:1, and which has a crystalline melting point not lower than 385° C. and an intrinsic viscosity of 0.7 to 2.0 dl/g (sulfuric acid at 25° C.).

11. The process according to claim 1, wherein said salt of the alkali metal is potassium carbonate, sodium carbonate, lithium carbonate, cesium carbonate, rubidium carbonate, potassium bicarbonate, sodium bicarbonate, potassium phosphate, sodium phosphate, potassium stannate, sodium stannate or mixtures thereof.

12. The process according to claim 5 wherein the catalyst is present in an amount of 0.1 to 100% by weight, based on the aromatic halogen compound.

13. The process according to claim 12, wherein the amount is 1 to 30% by weight.

14. The process according to claim 1, wherein the reacting is conducted in the presence of a solvent.

15. The process according to claim 1, wherein the solvent is a ketone, a sulfone, an ether, an amide, a hydrocarbon or a halogenated hydrocarbon.

16. The process according to claim 1, wherein the reacting is conducted at a temperature of from 150° C. to 400° C.

* * * * *